(12) United States Patent
Garretson et al.

(10) Patent No.: US 9,186,116 B2
(45) Date of Patent: *Nov. 17, 2015

(54) AUTOMATIC TOOL ALIGNMENT IN A BACKSCATTER X-RAY SCANNING SYSTEM

(71) Applicant: Sandia Corporation, Albuquerque, NM (US)

(72) Inventors: Justin Garretson, Albuquerque, NM (US); Clinton G. Hobart, Albuquerque, NM (US); Thomas S. Gladwell, Albuquerque, NM (US); Mark J. Monda, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/711,518

(22) Filed: May 13, 2015

(65) Prior Publication Data

US 2015/0247946 A1    Sep. 3, 2015

Related U.S. Application Data

(63) Continuation of application No. 13/336,146, filed on Dec. 23, 2011, now Pat. No. 9,055,886.

(60) Provisional application No. 61/429,781, filed on Jan. 5, 2011.

(51) Int. Cl.
*G01N 23/20* (2006.01)
*A61B 6/08* (2006.01)
*G01N 23/203* (2006.01)
(Continued)

(52) U.S. Cl.
CPC ... *A61B 6/08* (2013.01); *F41F 3/04* (2013.01); *G01N 23/203* (2013.01); *G01V 5/0025* (2013.01); *H01J 37/3045* (2013.01); *B64D 7/08* (2013.01); *F41C 27/06* (2013.01);
(Continued)

(58) Field of Classification Search
CPC ..... G01N 23/083; G01N 23/10; G01N 23/20; G01N 23/203; F42B 33/06; F41H 11/136; F41F 3/04; B64D 7/08; F41G 7/2293; F41C 27/06; G01V 5/008; G01V 5/0016; G01V 5/0025; H01J 37/304; H01J 37/3045
USPC ............... 378/65, 91, 98, 98.6, 146, 98.8, 378/162–164, 193–198, 204, 205, 207, 378/210; 600/407, 425–429
See application file for complete search history.

(56) References Cited

U.S. PATENT DOCUMENTS 5,022,062 A    6/1991    Annis
5,803,912 A    9/1998    Siczek et al.
(Continued)

*Primary Examiner* — Anastasia Midkiff
(74) *Attorney, Agent, or Firm* — Daniel J. Jenkins

(57) ABSTRACT

Technologies pertaining to backscatter x-ray scanning systems are described herein. The backscatter x-ray scanning system includes an x-ray source, which directs collimated x-rays along a plurality of output vectors towards a target. A detector detects diffusely reflected x-rays subsequent to respective collimated x-rays impacting the target, and outputs signals indicative of parameters of the detected x-rays. An image processing system generates an x-ray image based upon parameters of the detected x-rays, wherein each pixel in the image corresponds to a respective output vector. A user selects a particular portion of the image, and a medical device is positioned such that its directional axis is coincident with the output vector corresponding to at least one pixel in the portion of the image.

18 Claims, 8 Drawing Sheets

(51) Int. Cl.
  *H01J 37/304* (2006.01)
  *F41F 3/04* (2006.01)
  *G01V 5/00* (2006.01)
  *F41C 27/06* (2006.01)
  *G01N 23/10* (2006.01)
  *B64D 7/08* (2006.01)
  *F41H 11/136* (2011.01)
  *F42B 30/00* (2006.01)

(52) U.S. Cl.
  CPC .............. *F41H 11/136* (2013.01); *F42B 30/00* (2013.01); *G01N 23/10* (2013.01); *G01N 23/20* (2013.01)

(56) References Cited

U.S. PATENT DOCUMENTS

| | | |
|---|---|---|
| 6,321,106 B1 | 11/2001 | Lemelson |
| 7,505,562 B2 | 3/2009 | Dinca et al. |
| 7,508,910 B2 | 3/2009 | Safai et al. |
| 7,555,099 B2 | 6/2009 | Rothschild et al. |
| 7,593,510 B2 | 9/2009 | Rothschild |
| 8,479,435 B1 | 7/2013 | Gladwell et al. |
| 8,532,259 B2 | 9/2013 | Shedlock et al. |
| 9,055,886 B1 * | 6/2015 | Garretson et al. ................ 23/20 |
| 2004/0218714 A1 | 11/2004 | Faust |
| 2006/0245548 A1 | 11/2006 | Callerame et al. |
| 2008/0253522 A1 | 10/2008 | Boyden et al. |

* cited by examiner

AUTOMATIC TOOL ALIGNMENT IN A BACKSCATTER X-RAY SCANNING SYSTEM

RELATED APPLICATIONS

This application is a continuation of and claims priority to U.S. patent application Ser. No. 13/336,146, filed on Dec. 23, 2011, and entitled "Automatic Tool Alignment in a Backscatter X-Ray Scanning System", currently allowed, and to U.S. Provisional Patent Application No. 61/429,781, filed on Jan. 5, 2011, and entitled "AN APPROACH TO PRECISION AIM USING BACKSCATTER RADIOGRAPHY", the entireties of which are incorporated herein by reference.

STATEMENT OF GOVERNMENTAL INTEREST

This invention was developed under Contract DE-AC04-94AL85000 between Sandia Corporation and the U.S. Department of Energy. The U.S. Government has certain rights in this invention.

TECHNICAL FIELD

Aspects described herein are generally directed towards technologies pertaining to backscatter radiography. More particularly, aspects described herein pertain to aiming a medical device at a portion of a concealed target that is imaged using backscatter radiography.

BACKGROUND

Radiography involves the utilization of x-rays to view a non-uniformly composed material, such as the human body. By using the physical properties of x-rays, an image can be developed, wherein the image displays areas of a target that include different densities and compositions. An exemplary x-ray imaging system is a backscatter x-ray scanning system. Backscatter x-ray scanning systems are configured to direct narrow (collimated) beams of x-rays towards a target over respective output vectors, such that collimated x-rays in an x-ray beam impact the target. At least some of the x-rays will diffusely reflect upon impacting the target, and a detector detects the reflected x-rays. Intensity of a pixel can then be computed based upon parameters of the detected x-rays that have reflected from the target. To generate an image, an x-ray source directs collimated x-rays over a plurality of output vectors (e.g., performs a scan).

Backscatter x-ray scanning systems are particularly useful when it is difficult (or impossible) to position an x-ray source and a detector on opposing sides of a target. A conventional application of a backscatter x-ray scanning system occurs in airports, where human bodies are scanned to detect hidden weapons, liquids, narcotics, currency, and other contraband. Another application for a backscatter x-ray scanning system includes the scanning of large vehicles for contraband, as the utilization of a backscatter x-ray scanning system is much faster and less expensive when compared to performing physical searches.

SUMMARY

The following is a brief summary of subject matter that is described in greater detail herein. This summary is not intended to be limiting as to the scope of the claims.

Described herein are various technologies pertaining to a backscatter x-ray scanning system, and more particularly to aiming a tool at a particular position on a target responsive to receipt of selection of at least one pixel in an image of the target, wherein the image is generated by the backscatter x-ray scanning system. A backscatter x-ray scanning system includes an x-ray source that generates collimated x-rays over a plurality of output vectors towards a target. The backscatter x-ray scanning system also includes a detector that is co-located with the x-ray source, wherein the detector detects x-rays that are diffusely reflected by the target responsive to the collimated x-rays impacting the target. Parameters of x-rays detected by the detector are utilized to generate an x-ray image, wherein a pixel of the x-ray image corresponds to a respective output vector. Azimuth and elevation angles of vectors over which x-rays are output by the x-ray source alter when performing a scan. Image processing software is utilized to receive signals from the detector corresponding to collimated x-rays transmitted over different output vectors and to generate an image based upon such signals, wherein the image has a number of pixels equivalent to the number of output vectors.

In an exemplary embodiment, a resulting x-ray image of the target can be presented to a user on a display screen. The user may employ a user input mechanism, such as a touch sensitive display, a mouse, a microphone, or the like to identify a particular portion of the image corresponding to a region of interest of the target. A computing device that is programmed to control operation of at least one motor can receive the selection of the portion of the image from the user (by way of the user input mechanism) and, responsive thereto, transmits a signal to a motor that is operably coupled to a tool. For instance, the tool may be a medical instrument, a diffuser, or the like. The motor can cause the tool to be positioned such that a directional axis of the tool is coincident with an output vector that corresponds to a selected pixel in the image. In other words, the directional axis of the tool will be pointed at the portion of the target that corresponds to the selected pixel in the x-ray image.

In an exemplary embodiment, the x-ray source can output collimated x-rays from a single point (a first position) in three-dimensional space. Responsive to receiving a user selection of a pixel in an x-ray image, the computing device can transmit a signal to the motor that causes the motor to change the position of the x-ray source from the first position to a second position in three-dimensional space while positioning the tool at the first position. Subsequently, the directional axis of the tool can be aligned such that it is coincident with the output vector that is known to correspond to the selected pixel. Upon the directional axis of the tool being positioned coincident with the output vector corresponding to the selected pixel, the tool can engage the target. For instance, the tool may be a diffuser and the target may be an improvised explosive device (IED) that is concealed beneath the ground. The x-ray image of the concealed IED may be reviewed by a user who selects a particular portion of the IED that is desirably diffused. The diffuser is then aimed towards the target by placing the directional axis thereof on the output vector corresponding to the selected location of the IED in the x-ray image. The diffuser thereafter outputs a projectile that diffuses the IED. In another example, the tool may be a medical instrument that is configured to perform a medical procedure on a patient (the target). For example, the medical tool may be a scalpel, a source of electromagnetic radiation, etc. In such an example, the x-ray image may include an image of a cancerous region in a human body, and the tool can be aimed such that it is directed at the cancerous region.

Other configurations of backscatter x-ray scanning systems include an x-ray source that rasters vertically and/or horizontally. In such an embodiment, the one or more motors are operable to position the tool in three-dimensional space at the position of the x-ray source when the x-ray source output collimated x-rays that corresponds to a selected portion of an x-ray image. The directional axis of the tool can thereafter be positioned such that it is coincident with the output vector of the collimated x-rays. In another exemplary embodiment, it may be desirable to position the tool in front of or behind the x-ray source. In such an embodiment, one or more motors are operable to position the tool using at least four degrees of freedom. The position of the tool can be computed based at least in part upon a known or sensed distance between the tool and the x-ray source.

Other aspects will be appreciated upon reading and understanding the attached figures and description.

DETAILED DESCRIPTION

Figure 1:
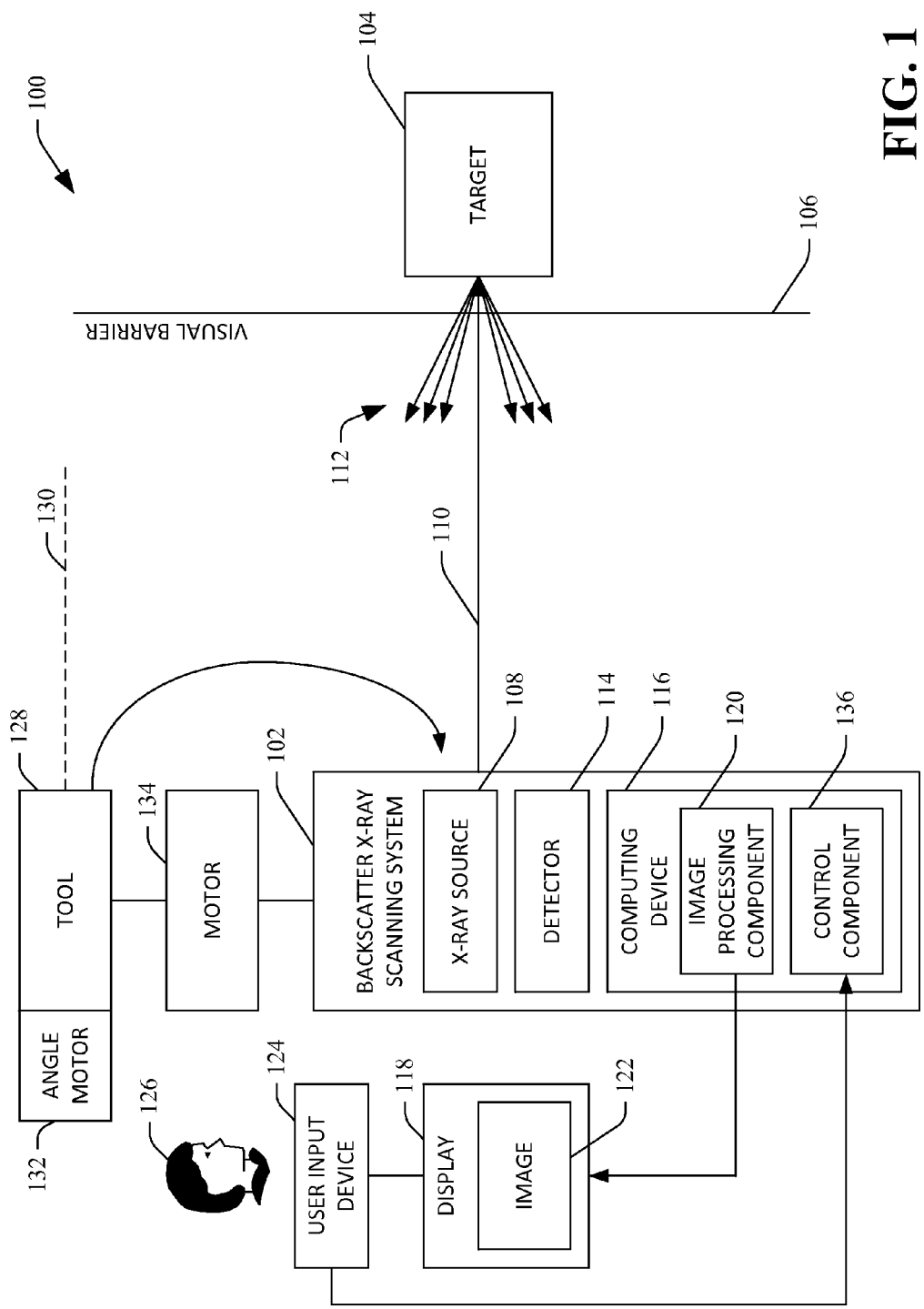
FIG. 1 is a functional block diagram of an exemplary system that facilitates aligning a directional access of a tool coincident with an output vector of collimated x-rays generated by an x-ray source in a backscatter x-ray scanning system.

Various technologies pertaining to backscatter x-ray scanning systems will now be described with reference to the drawings, where like reference numerals represent like elements throughout. In addition, several functional block diagrams of exemplary systems are illustrated and described herein for purposes of explanation; however, it is to be understood that functionality that is described as being carried out by certain system components may be performed by multiple components. Similarly, for instance, a component may be configured to perform functionality that is described as being carried out by multiple components. Additionally, as used herein, the term "exemplary" is intended to mean serving as an illustration or example of something, and is not intended to indicate a preference.

As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices.

With reference now to FIG. 1, an exemplary system 100 that facilitates positioning a tool such that its directional access intersects a target at a location that corresponds to a selected portion of an x-ray image of such target is illustrated. The system 100 comprises a backscatter x-ray scanning system 102 that is configured to generate an x-ray image of a target 104 that is concealed by a visual barrier 106. In an exemplary embodiment, the target 104 may be a weapon, such as an improvised explosive device (IED) or mine that is placed underground such that it is not visible. In another exemplary embodiment, the target 104 may be human body tissue, such as bone, an organ, a tumor, etc.

The backscatter x-ray scanning system 102 includes an x-ray source 108 that transmits collimated x-rays along an output vector 110 towards the target 104. In an exemplary embodiment, the x-ray source 108 may be a point source, such the x-ray source 108 is stationary in three-dimensional space when the backscatter x-ray scanning system 102 is performing a scan. The scan is undertaken by altering azimuth and elevation angles of output vectors of collimated x-rays transmitted from the x-ray source 108. In other exemplary embodiments, during a scan the x-ray source 108 may have at least one degree of freedom corresponding thereto, such that the x-ray source can raster either horizontally or vertically. For instance, the x-ray source 108 may transition directionally along a first axis while the elevation angle of collimated x-rays is modified. In still yet another exemplary embodiment, the x-ray source 108 may be transitionable along two or more axes.

The backscatter x-ray scanning system 102 further includes a detector 114. For each output vector over which the x-ray source 108 emits collimated x-rays, the detector 114 detects respective diffusely reflected x-rays 112 and outputs a signal that is indicative of parameters of the reflected x-rays 112. Such parameters may be or include attenuation of the reflected x-rays 112, magnitude of the reflected x-rays 112, location(s) on the detector 114 where the reflected x-rays 112 impact the detector 114, amongst other parameters.

The backscatter x-ray scanning system 102 further comprises a computing device 116 that receives signals from the detector 114 and generates an x-ray image of the target 104 based at least in part upon such received signals. With more specificity, the system 100 comprises a display 118 that is in communication with the computing device 116. The display 118 is shown as being separate from the backscatter x-ray scanning system 102; it is to be understood, however, that in other exemplary embodiments, the display 118 can be included as a portion of the backscatter x-ray scanning system 102. The computing device 116 comprises an image processing component 120, which generates an x-ray image 122 that is displayed on the display 118. In operation, the image processing component 120 receives signals from the detector 114 and generates the x-ray image 122 based at least in part upon such received signals, wherein each pixel in the x-ray image 122 corresponds to a particular output vector over which collimated x-rays are emitted from the x-ray source 108.

Accordingly, the x-rays on the output vector 110 correspond to a particular pixel in the x-ray image 122. The image processing component 120 computes intensities for pixels that correspond to a respective plurality of output vectors and generates the image 122 such that the image 122 comprises the plurality of pixels with the computed intensity values. The correspondence of pixels in the image 122 to elevation and azimuth angles of output vectors (from a reference point) can be known and retained in computer-readable storage of the computing device 116.

The system 100 further comprises a user input device 124 that accepts input from a user 126. Thus, the user input device 124 may be a mouse, a touch sensitive display, a microphone that receives voice commands, or other suitable user input device.

The user 126 reviews the x-ray image 122 displayed on the display 118 and selects a portion of such x-ray image 122. For example, the user 126 can select at least one pixel in the x-ray image 122, wherein the at least one pixel corresponds to a particular position of the target 104 relative to the backscatter x-ray scanning system 102. In some embodiments, the user 126 may select a region of the x-ray image 122 that comprises a plurality of pixels. A particular pixel can be selected from the plurality of pixels utilizing any suitable technique; for instance, a most central pixel amongst the plurality of pixels can be selected.

The system 100 further comprises a tool 128 that has a directional axis 130. In an example, the tool 128 may be a diffuser that is configured to output a projectile responsive to receiving a command from the user 126. In another example, the tool 128 may be a medical instrument that is configured to perform a medical operation on the target 104 responsive to receiving a command from the user 126. For instance, the tool 128 may be a scalpel or laser that is configured to perform an incision on the target 104. In yet another example, the tool 128 may be a source of electromagnetic radiation that is desirably directed towards a particular region of a patient (an organ). The system 100 further comprises an angle motor 132 that is operably coupled to the tool 128. The angle motor 132 can be configured to alter elevation and/or azimuth angle of the directional axis 130 of the tool 128 (e.g., tilt and pan the directional axis 130 of the tool 128).

The system 100 additionally comprises a motor 134 that is operably connected to the tool 128, wherein the motor 134 is configured to alter a position of the tool 128 in three-dimensional space. For example, the tool 128 can be placed on a frame, and the motor 134 can cause the position/configuration of the frame to change, thereby changing the position of the tool 128 in a three-dimensional coordinate system.

The computing device 116 can additionally comprise a control component 136 that receives a signal from the user input device 124, wherein the signal identifies at least one pixel in the image 122 that has been selected by the user 126. Based upon known parameters of the backscatter x-ray scanning system 102, the control component 136, responsive to receiving the signal from the user input device 124, can determine a location (origin) of the x-ray source 108 in three-dimensional space (relative to a reference point) and elevation and azimuth angles of the output vector corresponding to the selected at least one pixel. If the x-ray source 108 is a point source, the location of the x-ray source 108 in three-dimensional space will remain constant. Subsequent to the location of the x-ray source 108, elevation angle of the output vector, and azimuth angle of the output vector being ascertained, the control component 136 outputs a control signal to the angle motor 132 and/or the motor 134 that causes the motor(s) 132 and/or 134 to position the tool 128 such that the directional axis 130 of the tool 128 is coincident with the output vector (e.g., the vector 110). In other words, the directional axis of the tool 130 will be aimed at a point on the target 104 that is selected by the user 126 via selecting a portion of the x-ray image 122 through utilization of the user input device 124.

As indicated above, in an exemplary embodiment, the x-ray source 108 may be a point source x-ray source, such that all x-rays emitted from the x-ray source during a scan originate from a single point in three-dimensional space (a first position). In such an embodiment, subsequent to the backscatter x-ray scanning system 102 performing a scan of the target 104 and the user 126 selecting at least one pixel in the image 122, the control component 136 can cause the motor 134 to transition the x-ray source 108 from the first position to a second position in three-dimensional space, and can further cause the tool 128 to be positioned at the first position. The control component 136 may also transmit a signal to the angle motor 132 that causes the angle motor 132 to alter the azimuth angle and elevation angle of the directional axis 130 of the tool 128 such that the directional axis 130 of the tool 128 is coincident with the output vector. Thereafter, either automatically or responsive to input from the user 126, the tool 128 can engage the target 104.

In another exemplary embodiment, either the x-ray source 108 may not be a point source or it may be desirable to position the tool 128 in front of or behind the x-ray source 108 such that the tool 128 is disposed between the x-ray source 108 and the target 104 or the x-ray source 108 is disposed between the tool 128 and the target 104. In such embodiments, a frame coupled to the tool 128 must allow the motor 134 and/or the angle motor 132 to position the tool 128 using at least four degrees of freedom (e.g., horizontally, vertically, elevation angle, and azimuth angle). In an embodiment where the x-ray source 108 is not a point source, but instead rasters vertically and/or horizontally when scanning the target 104, the motor 134 can be configured to allow placement of the tool 128 such that the tool 128 is transitioned to a position of the x-ray source 108 when the x-ray source emitted collimated x-rays over the output vector that corresponds to the at least one selected pixel.

In other embodiments, rather than the user 126 selecting at least one pixel, a computer-executable application can be configured to analyze the image 122 and automatically select at least one pixel therein. For instance, the computer-executable application can analyze intensity values of pixels to recognize the target 104, and can further analyze intensity values of pixels to select a particular portion of the target 104 in the image 122.

Exemplary applications of the system 100 will now be described. These applications are exemplary in nature and not intended to be limiting as to the scope of the hereto-appended claims. The system 100 may be a stationary system that is configured to scan targets that are positioned relative to the backscatter x-ray scanning system 102. For example, the target 104 may be concealed in a piece of luggage that is positioned in front of the system 100 by way of a conveyor, wherein it is desirable to ascertain if any weapons, contraband, or the like is hidden in such luggage. In such an application, the user 126 can review the x-ray image 122 to ascertain if a target of interest is inside the luggage and, if so, can direct the tool 128 (which may be a diffuser) to diffuse the weapon.

In another exemplary application, the target 104 may be an organ or other portion of a human body that is desirably subjected to a medical procedure. In such an application, the tool 128 may be a medical instrument, such as a source of electromagnetic radiation, a laser, a scalpel, etc. The user 126 can review the portion of the human body by way of the image 122, and can aim the tool 128 towards a desired position on the target 104 by interacting with the x-ray image 122. The user 126 may then cause the tool 128 to perform a medical procedure upon the directional axis 130 of the tool 128 being aimed as desired relative to the target 104.

In still yet another exemplary application, the backscatter x-ray scanning system 102 may be placed upon a movable robot that is configured to search for concealed explosive devices. Accordingly, the user 126 can direct the robot to a desired position and can direct the backscatter x-ray scanning system 102 to generate x-ray images of targets beneath the earth. If the backscatter x-ray scanning system 102 generates an image that shows existence of an explosive device, then the user 126 can align the directional axis 130 of the tool 128 to a particular point on the target 104 by interacting with the x-ray image 122 as described above. The user 126 may then cause the tool 128 to output a projectile to diffuse the explosive device. These and other applications are contemplated by the inventors and are intended to fall under the scope of the hereto-appended claims.

Figure 2:
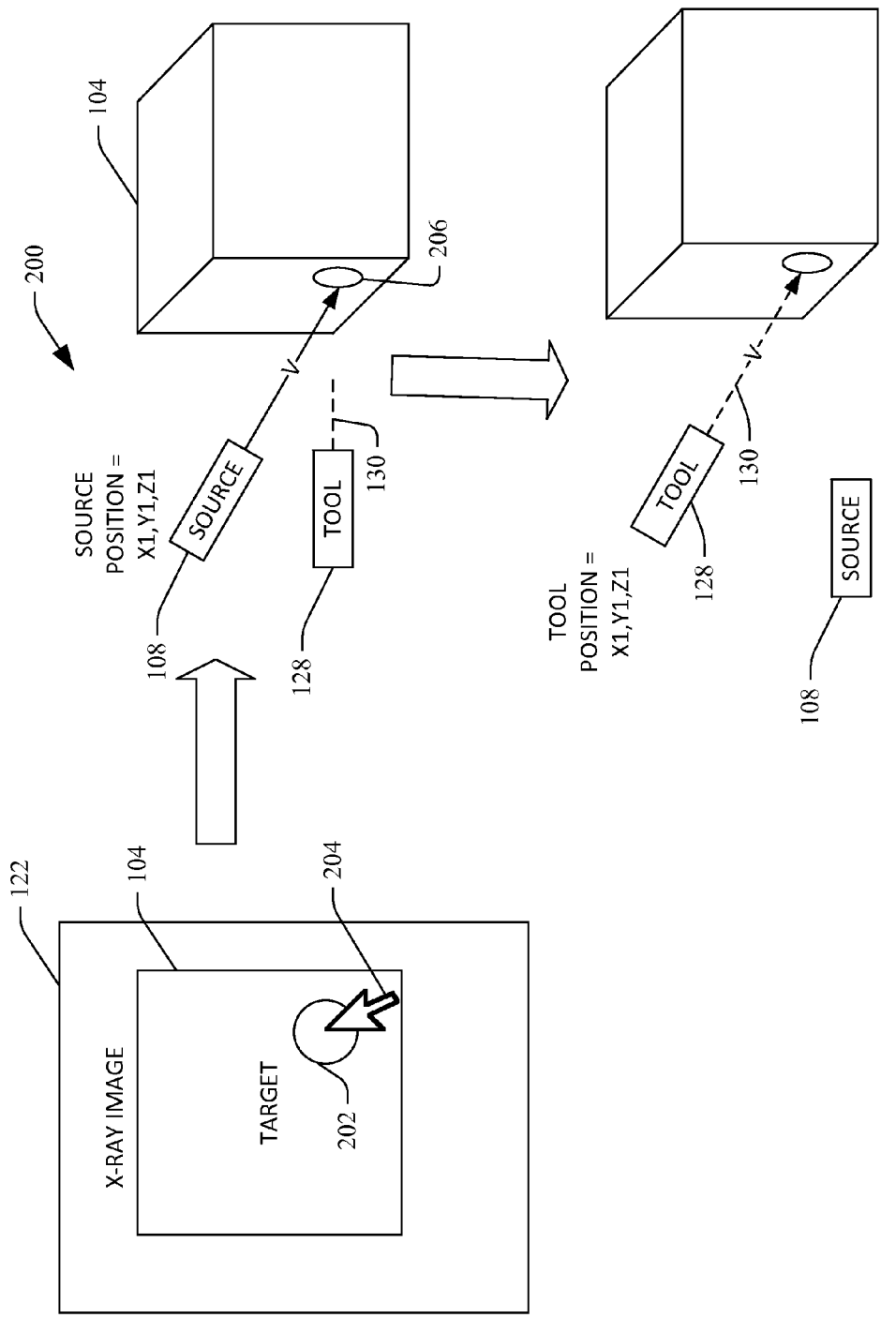
FIG. 2 is a diagram that illustrates the co-location of an x-ray source and a tool in connection with causing a directional axis of the tool to be coincident with an output vector of collimated x-rays generated at an x-ray source that correspond to a selected portion of an x-ray image.

With reference now to FIG. 2, an exemplary depiction 200 of positioning of a tool relative to the target 104 is illustrated. The x-ray image 122 includes an image of at least a portion of the target 104. The user 126 can select a particular point 202 of the target 104 in the x-ray image 122, for example, by utilizing a cursor 204 and selecting the point 202 with the cursor 204. As described above, the point 202 in the x-ray image 122 corresponds to a point 206 on the target 104, and such point 202 in the x-ray image 122 corresponds to a particular output vector V. The correspondence between the output vector and the pixel can be known based on intrinsic parameters of the backscatter x-ray scanning system 102. In the exemplary depiction 200, the x-ray source 108 is a point source such that the x-ray source 108 remains at a first position $(X_1, Y_1, Z_1)$ during a scan. The tool 128 can be in a second position in three-dimensional space $(X_2, Y_2, Z_2)$.

Subsequent to the user selecting the point 202 in the x-ray image 122, the control component 136 outputs a signal to the motor 134, and the motor 134 transitions the x-ray source 108 to a third position in three-dimensional space. The motor 134 additionally causes the tool 128 to be positioned at the first position $(X_1, Y_1, Z_1)$. It is to be understood that the control component 136 can also cause the motor 134 to place the x-ray source 108 at the second position. As the tool 128 is located at the first position, the angle motor 132 can be employed to align the directional axis 130 of the tool (set the elevation angle and azimuth angle) to the point 206 on the target 104 without ascertaining distance between the tool 128 and the point 206. Instead, the directional the axis 130 of the tool 128 is coincident with the output vector V of the source 108 that corresponds to the selected point 202 in the x-ray image 122.

Figure 3:
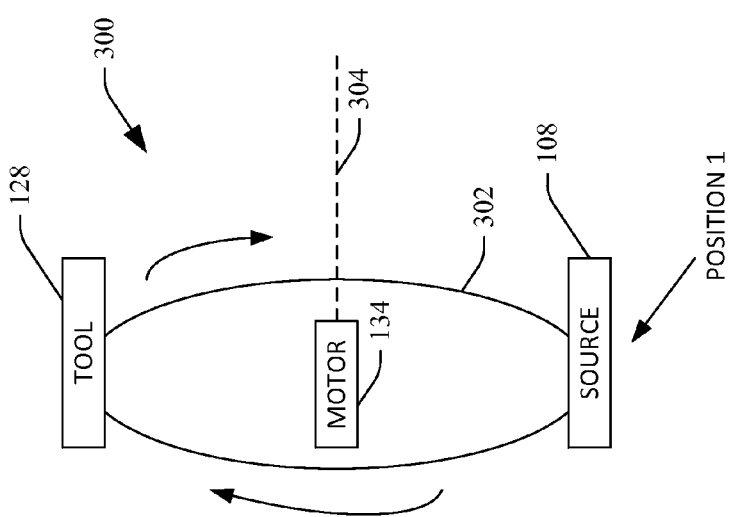
FIG. 3 is a diagram of an exemplary frame that can be used to cause a tool to be co-located with an x-ray source in three-dimensional space.

Now referring to FIG. 3, an exemplary configuration 300 that can allow the tool 128 to be co-located with the x-ray source 108 is illustrated. The configuration 300 includes an elliptical frame 302, wherein the x-ray source 108 and the tool 128 are mounted on the elliptical frame 302. The x-ray source 108 is initially located at a first position in three-dimensional space. The motor 134 is operably coupled to the elliptical frame 302, and can cause the elliptical frame 302 to rotate about an axis 304. The x-ray source 108 performs a scan while located at the first position, and an x-ray image is generated based upon the scan. Subsequently, the user 126 interacts with the resulting image, requesting that the tool 128 be aimed towards a particular point on the target 104. The control component 136 transmits a signal to the motor 134, causing the motor to rotate the elliptical frame 302 about the axis 304 until the tool 128 resides in the first position (and the x-ray source 108 is moved out of the first position). The configuration 300 is exemplary and is intended to illustrate but one possible configuration for locating the tool 128 at the scan position of the x-ray source 108.

Figure 4:
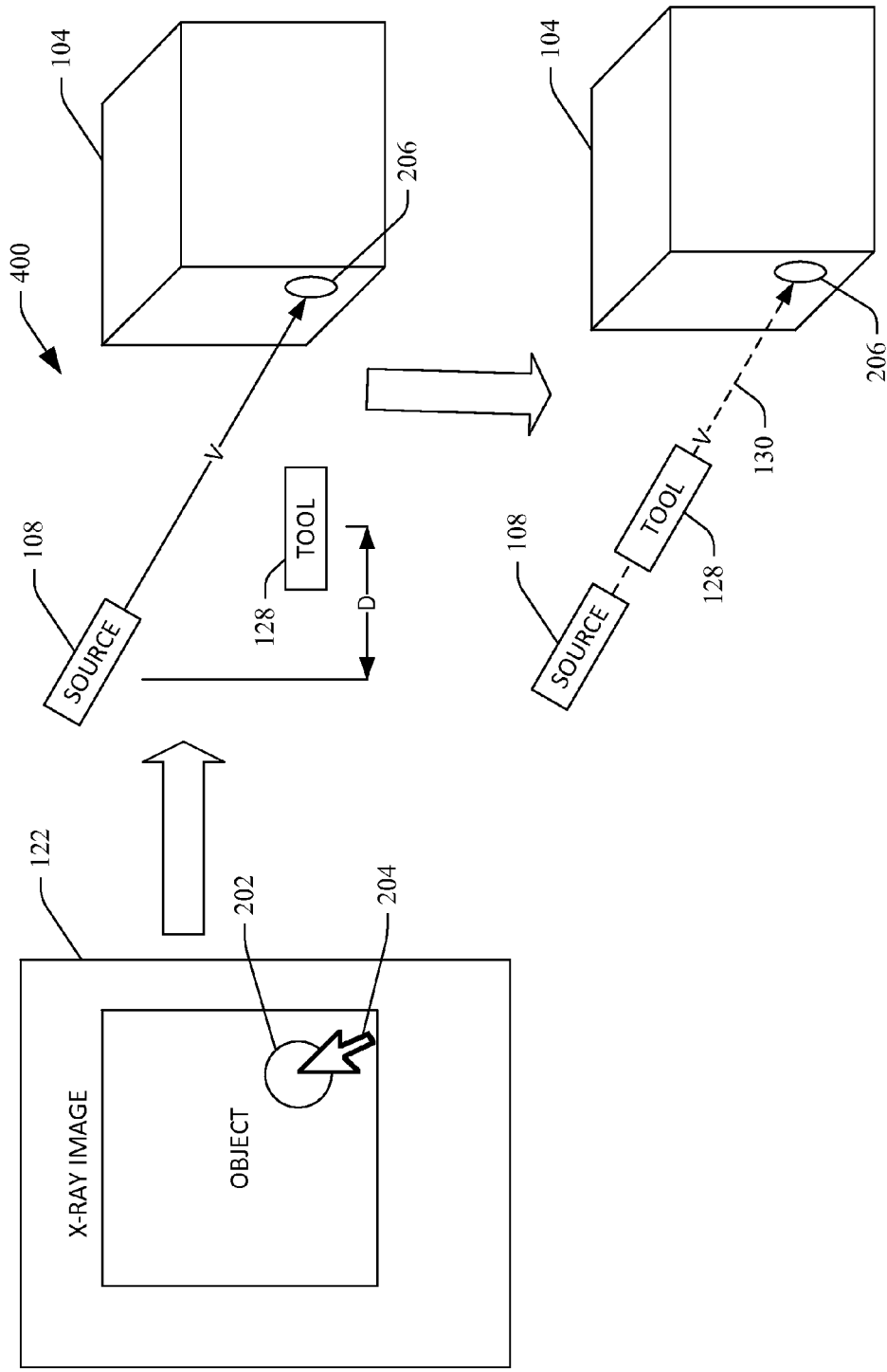
FIG. 4 is a diagram that illustrates the positioning of a tool such that a directional axis thereof is coincident with an output vector of collimated x-rays generated by an x-ray source for a selected portion of an x-ray image.

With reference now to FIG. 4, an exemplary depiction 400 of positioning the tool 128 such that its directional axis 130 is coincident with an output vector V that corresponds to the selected point 202 in the x-ray image 122 is illustrated. As described above, the user 126 selects the point 202 in the x-ray image 122. The control component 136, responsive to receiving the selection from the user 126, causes the motor 134 and the angle motor 132 to position the tool 128 such that the directional axis 130 is coincident with the output vector V. In such depiction, the tool 128 is desirably positioned in front of or behind the x-ray source 108 relative to the target 104. Accordingly, at least four degrees of freedom are needed to position the tool 128 (horizontal, vertical, azimuth angle, and elevation angle). The control component 136, when generating the signal for transmittal to the motor 134 (and the angle motor 132), can consider various factors to correctly position the tool 128, such as an initial location of the x-ray source 108, an initial location of the tool 128, distance D of the vector between the x-ray source 108 and the tool 128, etc. In an exemplary embodiment, the control component 136 causes the motor 134 to position the tool 128 between the source 108 and the target 104. In other embodiments, the control component 136 can position the tool 128 such that the x-ray source 108 is between the tool 128 and the target 104.

Figure 5:
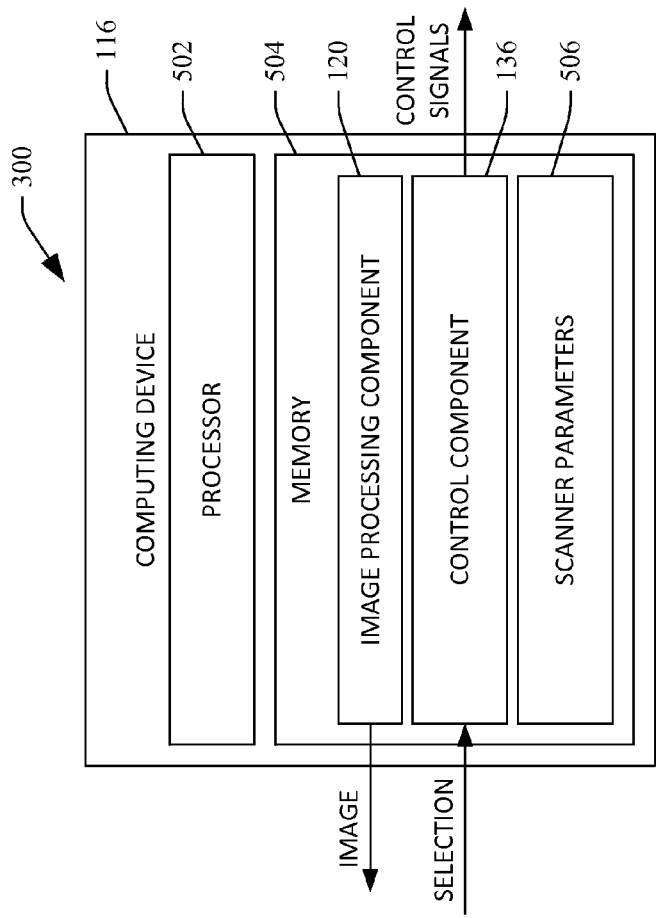
FIG. 5 is an exemplary computing device that comprises computer executable instructions for transmitting signals to a motor, the signals causing the motor to position a directional axis of a tool coincident with an output vector of collimated x-ray beams generated by an x-ray source that correspond to a pixel selected from an x-ray image.

With reference now to FIG. 5, the computing device 116 is shown. The computing device 116 comprises a processor 502 and a memory 504, wherein the memory 504 includes instructions that are executable by the processor 502. In an example, the memory 504 may be RAM, ROM, EEPROM, Flash memory, or other suitable computer readable storage.

The memory 504 includes the image processing component 120 that receives signals from the detector 114 and generates an x-ray image responsive to receipt of such signals. The memory 504 also comprises the control component 136 that receives a signal from the user input device 124 that indicates that the user 126 has selected at least one pixel in the x-ray image generated by the image processing component 120. The memory 504 further includes scanner parameters 506, wherein the scanner parameters 506 are indicative of a relation between pixels in the image generated by the image processing component 120 and corresponding output vectors over which collimated x-rays are transmitted by the x-ray source 108. The control component 136, responsive to receiving a selection of at least one pixel in the image 122, can access the scanner parameters 506 to ascertain azimuth and elevation angles of the output vector (relative to a reference point) corresponding to the at least one selected pixel, and can output control signals to the motor 134 and/or the angle motor 132 responsive to accessing the scanner parameters 506.

Figure 6:
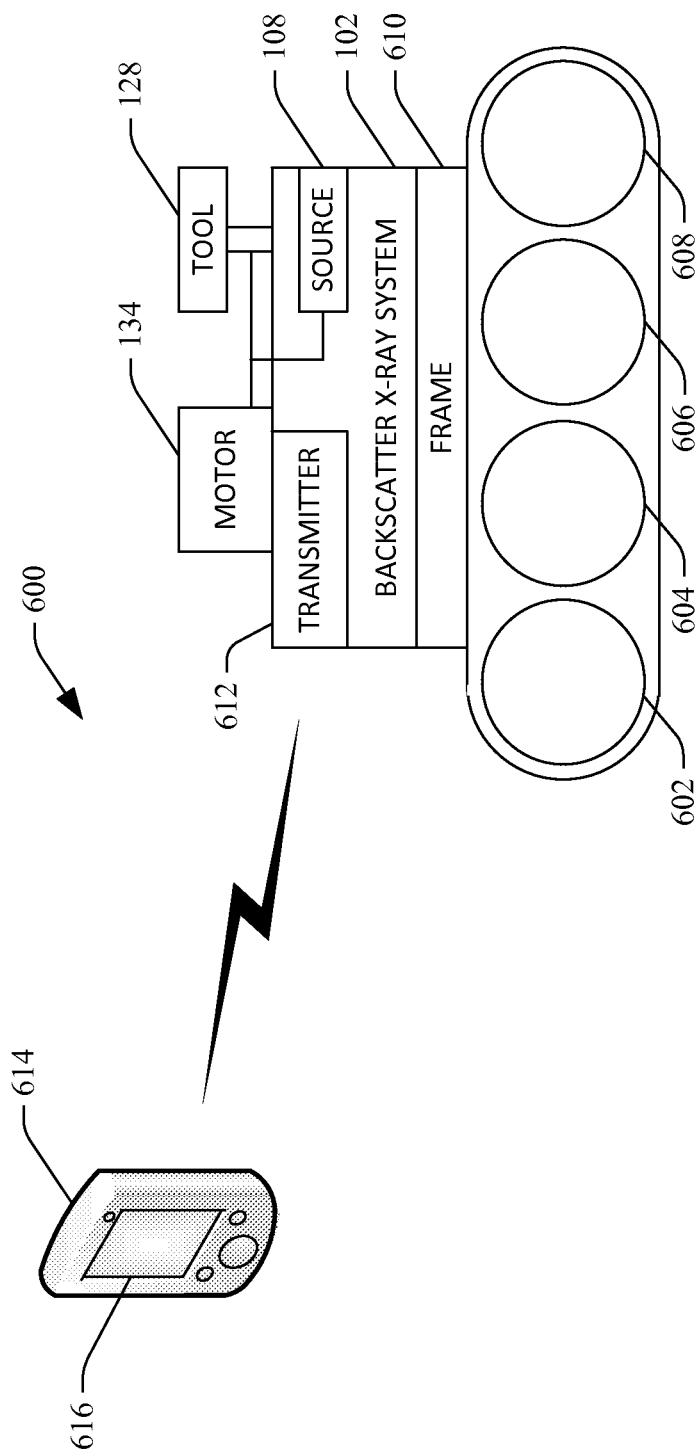
FIG. 6 illustrates an exemplary robot that comprises a backscatter x-ray scanning system.

Turning now to FIG. 6, an exemplary robot 600 that includes the backscatter x-ray scanning system 102 is illustrated. The robot 600 comprises wheels 602-608 that are driven by a motor (not shown). In an example, the wheels 602-608 can be controlled via a remote control device and/or can be automatically controlled through utilization of computer executable code installed on a computing device included in the robot 600. The robot 600 includes a frame 610 that supports the backscatter x-ray scanning system 102. In an exemplary embodiment, the x-ray source 108 in the backscatter x-ray scanning system 102 can be configured to perform a scan of a particular area responsive to receipt of a command from a remotely located user. In another exemplary embodiment, the backscatter x-ray scanning system 102 can be configured to continuously perform scans as the robot 600 transitions to different locations.

The backscatter x-ray scanning system 102 also includes a transmitter 612 that can wirelessly transmit images to a remotely located computing device 614. The computing device 614 includes a display 616, wherein a user can review x-ray images generated by the backscatter x-ray scanning system 102 on the display 616. If the user wishes to cause the tool 128 to be aimed at a particular point of a scanned target, the user can select the point corresponding to the target as shown in the image on the display screen 616 by way of a user input mechanism. Such selection can be transmitted back to the robot 600 by way of the transmitter 612. The control component 136 (not shown) may then output a control signal to the motor 134 and the angle motor 132 that causes the motors 132 and 134 to position the tool 128 such that the directional axis 130 of the tool is coincident with the output vector of collimated x-rays emitted by the x-ray source 108 that corresponds to at least one selected pixel in the image shown on the display 616. The user may then remotely cause the tool 128 to engage the target, for instance, by causing a signal to be transmitted from the remotely located computing device 614 back to the tool 128 by way of the transmitter 612.

Figure 7:
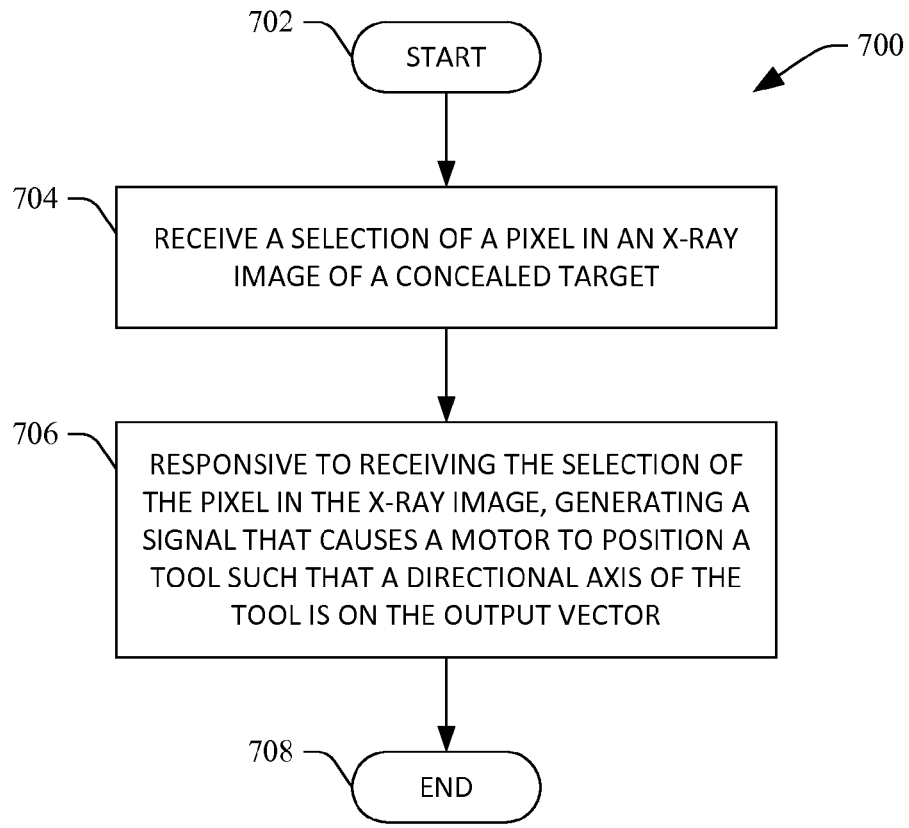
FIG. 7 is a flow diagram that illustrates an exemplary methodology for generating a signal that causes a motor to position a tool such that a directional axis of the tool is coincident with an output vector of collimated x-rays that correspond to a selected pixel in an x-ray image.
Figure 8:
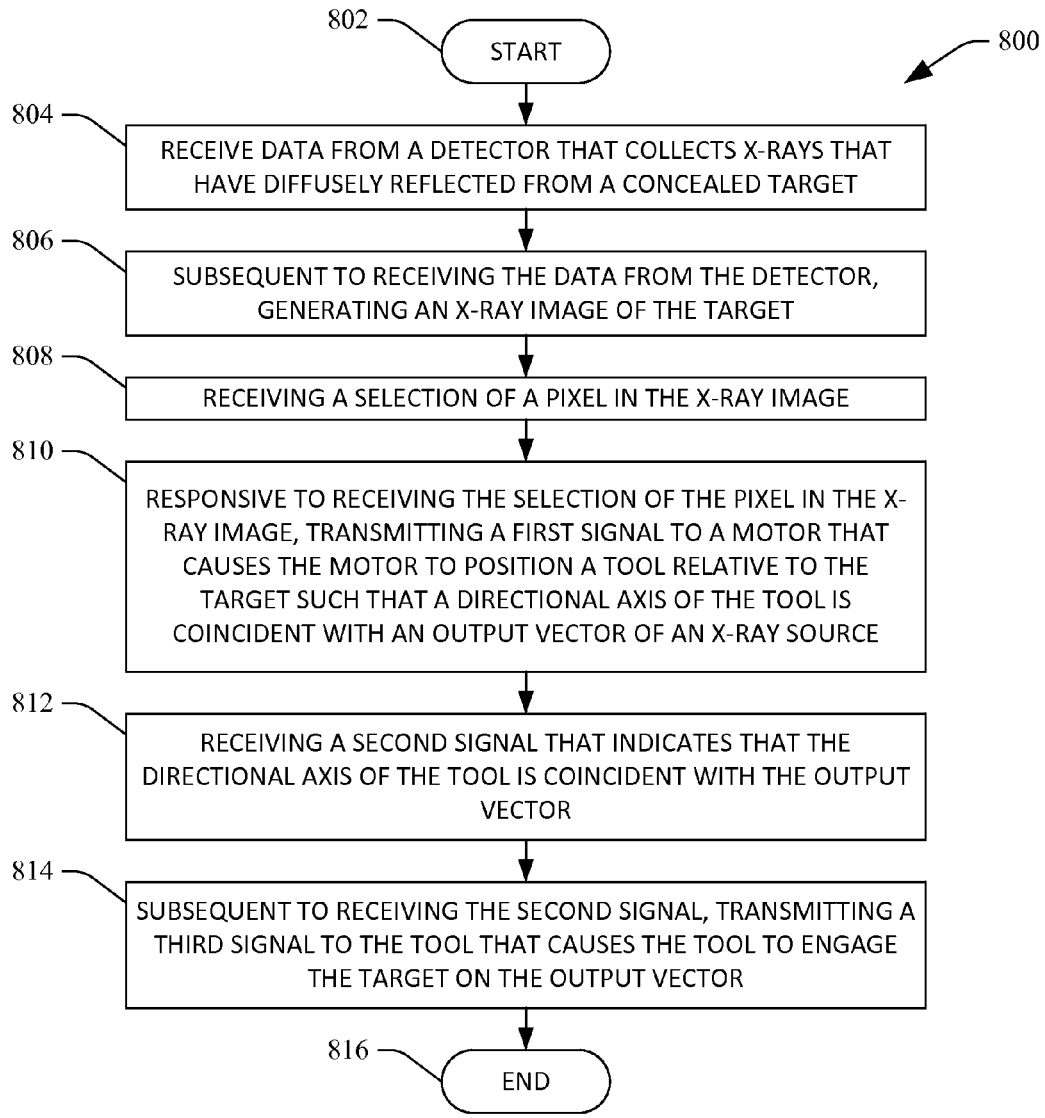
FIG. 8 is a flow diagram that illustrates an exemplary methodology for causing a tool to engage a target along a vector that is coincident with an output vector of an x-ray source that corresponds to a selected pixel in an x-ray image.

With reference now to FIGS. 7-8, various exemplary methodologies are illustrated and described. While the methodologies are described as being a series of acts that are performed in a sequence, it is to be understood that the methodologies are not limited by the order of the sequence. For instance, some acts may occur in a different order than what is described herein. In addition, an act may occur concurrently with another act. Furthermore, in some instances, not all acts may be required to implement a methodology described herein.

Moreover, the acts described herein may be computer-executable instructions that can be implemented by one or more processors and/or stored on a computer-readable medium or media. The computer-executable instructions may include a routine, a sub-routine, programs, a thread of execution, and/or the like. Still further, results of acts of the methodologies may be stored in a computer-readable medium, displayed on a display device, and/or the like. The computer-readable medium may be any suitable computer-readable storage device, such as memory, hard drive, CD, DVD, flash drive, or the like. As used herein, the term "computer-readable medium" is not intended to encompass a propagated signal.

Referring now to FIG. 7, an exemplary methodology 700 that facilitates generating a control signal that causes a motor to position a tool such that a directional axis of the tool is coincident with an output vector over which collimated x-rays from an x-ray source are directed towards a target is illustrated. The methodology 700 starts at 702, and at 704 a selection of a pixel in an x-ray image of a concealed target is received. As described above, the x-ray image is generated by a backscatter x-ray scanning system, and a location of the pixel in the x-ray image corresponds to a particular output vector over which collimated x-rays generated by the x-ray score source travel during a scan undertaken by the backscatter x-ray scanning system.

At 706, responsive to receiving the selection of the pixel in the x-ray image, a control signal is generated that causes a motor to position a tool such that a directional axis of the tool is coincident with the output vector. The methodology completes at 708.

Now referring to FIG. 8, an exemplary methodology 800 for causing a tool to engage a particular point of a target is illustrated. The methodology 800 starts at 802, and at 804 data from a detector that detects x-rays that have diffusely reflected from a concealed target are received. The detected x-rays are originated by an x-ray source that directs collimated x-rays along an output vector towards the concealed target.

At 806, subsequent to receiving the data from the detector, an x-ray image of the target is generated. The x-ray image of the target includes a pixel that has an intensity that is a function of the data received from the detector. Additionally, a location of the pixel in the image is known to correspond to the vector (the azimuth and elevation angles of the vector from a reference point).

At 808, a selection of the pixel in the x-ray image is received by way of a user input activism, and at 810, responsive to receiving the selection of the pixel in the x-ray image, a first signal is transmitted to a motor, wherein the first signal causes the motor to position a tool relative to the target such that a directional axis of the tool is coincident with the aforementioned vector. Accordingly, the directional axis of the tool is pointed towards a point on the target that corresponds to the selected pixel in the image.

At 812, a second signal is received, wherein the second signal indicates that the directional axis of the tool is coincident with the output vector. That is, a sensor can sense when the tool is in the desired position and can output a signal responsive to sensing that the tool is in the desired position.

At 814, subsequent to receiving the second signal, a third signal can be transmitted to the tool that causes the tool to engage the target, such that the tool engages the target at a location thereon that corresponds to the selected pixel in the x-ray image. For example, the tool may be a diffuser that outputs a projectile along the vector. The methodology 800 completes at 816.

Figure 9:
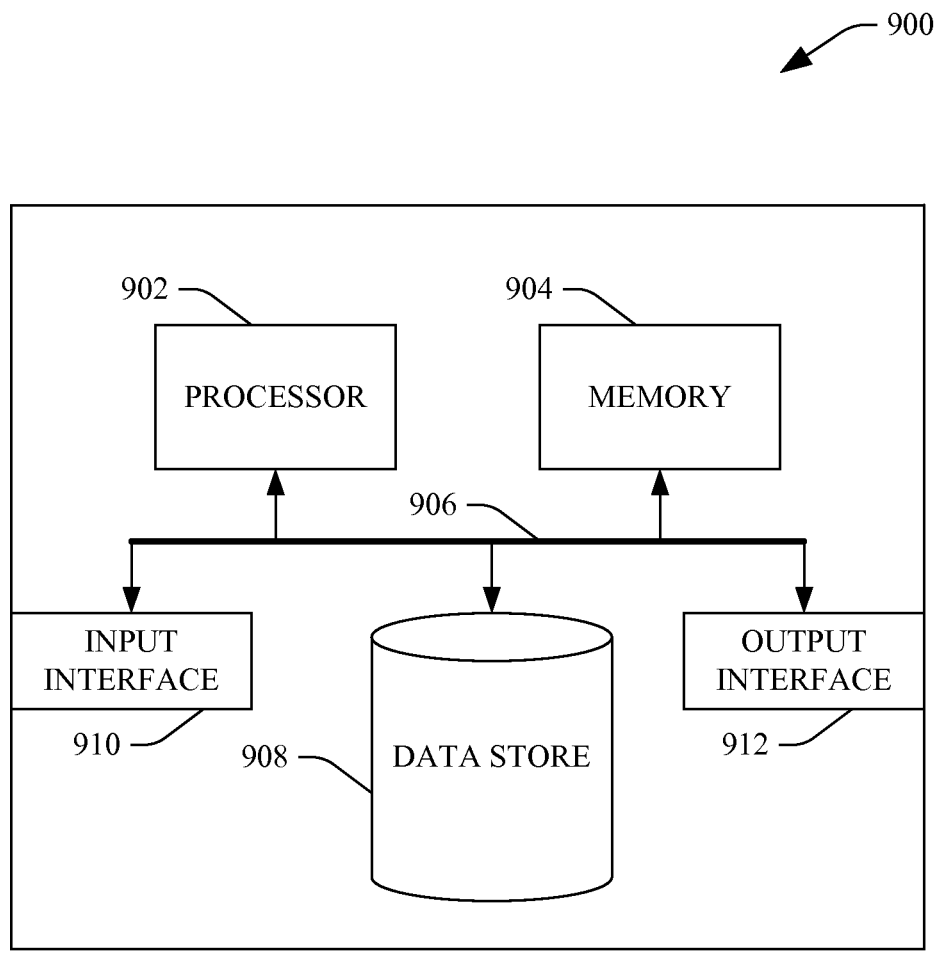
FIG. 9 is an exemplary computing system.

Now referring to FIG. 9, a high-level illustration of an exemplary computing device 900 that can be used in accordance with the systems and methodologies disclosed herein is illustrated. For instance, the computing device 900 may be used in a system that supports generating an x-ray image. In another example, at least a portion of the computing device 900 may be used in a system that supports generating control signals for transmittal to a motor, wherein the control signals are configured to position a tool relative to a target. The computing device 900 includes at least one processor 902 that executes instructions that are stored in a memory 904. The memory 904 may be or include RAM, ROM, EEPROM, Flash memory, or other suitable memory. The instructions may be, for instance, instructions for implementing functionality described as being carried out by one or more components discussed above or instructions for implementing one or more of the methods described above. The processor 902 may access the memory 904 by way of a system bus 906. In addition to storing executable instructions, the memory 904 may also store backscatter x-ray scanning system parameters, image data, etc.

The computing device 900 additionally includes a data store 908 that is accessible by the processor 902 by way of the system bus 906. The data store may be or include any suitable computer-readable storage, including a hard disk, memory, etc. The data store 908 may include executable instructions, backscatter x-ray scanning system parameters, image data, etc. The computing device 900 also includes an input interface 910 that allows external devices to communicate with the computing device 900. For instance, the input interface 910 may be used to receive instructions from an external computer device, a user, etc. The computing device 900 also includes an output interface 912 that interfaces the computing device 900 with one or more external devices. For example, the computing device 900 may display text, images, etc. by way of the output interface 912.

Additionally, while illustrated as a single system, it is to be understood that the computing device 900 may be a distributed system. Thus, for instance, several devices may be in communication by way of a network connection and may collectively perform tasks described as being performed by the computing device 900.

It is noted that several examples have been provided for purposes of explanation. These examples are not to be construed as limiting the hereto-appended claims. Additionally, it may be recognized that the examples provided herein may be permutated while still falling under the scope of the claims.

What is claimed is:

1. A method comprising:
   receiving a selection of a pixel in an x-ray image of a concealed target, the x-ray image generated by a backscatter x-ray scanning system, a location of the pixel in the x-ray image corresponding to an output vector over which an x-ray source in the backscatter x-ray scanning system transmits collimated x-rays; and
   responsive to receiving the selection of the pixel in the x-ray image, generating a signal that causes an angle motor to position a tool such that a directional axis of the tool is coincident with the output vector.

2. The method of claim 1, wherein the selection of the pixel in the x-ray image is received from a computer-executable program that automatically selects the pixel based at least in part upon an intensity of the pixel.

3. The method of claim 1, wherein the selection of the pixel in the x-ray image is received from a user input device.

4. The method of claim 1, further comprising:
   responsive to generating the signal, transmitting a second signal that causes the tool to engage the target.

5. The method of claim 4, wherein the tool is a diffuser, and wherein the operation comprises directing a projectile from the diffuser towards a portion of the target that corresponds to the pixel.

6. The method of claim 1, wherein the x-ray source is located at a first location in three-dimensional space, and wherein the signal causes the x-ray source to transition to a second location in three-dimensional space and causes the tool to be transitioned to the first location.

7. The method of claim 1, wherein the x-ray source and the tool are attached to a moveable robot.

8. The method of claim 1, wherein the motor positions the tool on the vector between the x-ray source and the target.

9. The method of claim 1, wherein the tool is a medical instrument.

10. A method comprising:
    receiving a selection of a pixel in an x-ray image of a concealed target, the x-ray image generated by a backscatter x-ray scanning system, a location of the pixel in the x-ray image corresponding to an output vector over which an x-ray source in the backscatter x-ray scanning system transmits collimated x-rays; and
    responsive to receiving the selection of the pixel in the x-ray image, generating a signal that causes an angle motor to position a medical instrument such that a directional axis of the medical instrument is coincident with the output vector.

11. The method of claim 10, wherein the selection of the pixel in the x-ray image is received from a computer-executable program that automatically selects the pixel based at least in part upon an intensity of the pixel.

12. The method of claim 10, wherein the selection of the pixel in the x-ray image is received from a user input device.

13. The method of claim 10, further comprising:
    responsive to generating the signal, transmitting a second signal that causes the medical instrument to engage the target.

14. The method of claim 10, wherein the x-ray source is located at a first location in three-dimensional space, and wherein the signal causes the x-ray source to transition to a second location in three-dimensional space and causes the medical instrument to be transitioned to the first location.

15. The method of claim 10, wherein the x-ray source and the medical instrument are attached to a moveable robot.

16. The method of claim 10, wherein the motor positions the medical instrument on the vector between the x-ray source and the target.

17. The method of claim 10, wherein the medical instrument is a laser or scalpel.

18. A computer-readable medium comprising instructions that, when executed by a processor, cause the processor to perform acts comprising:
    receiving data from a detector that detects x-rays that have diffusely reflected from a concealed target, the x-rays originating from an x-ray source that directs collimated x-rays on a vector towards the concealed target;
    subsequent to receiving the data from the detector, generating an x-ray image of the target, wherein the x-ray image comprises a pixel with an intensity that is based upon the data received from the detector, wherein a location of the pixel in the image corresponds to the vector;
    receiving a selection of the pixel in the x-ray image;
    responsive to receiving the selection of the pixel in the x-ray image, transmitting a first signal to a motor that causes the motor to position a medical instrument such that a directional axis of the medical instrument is coincident with the output vector.

\* \* \* \* \*